United States Patent
Carvalho et al.

(10) Patent No.: US 8,277,428 B2
(45) Date of Patent: Oct. 2, 2012

(54) SANITARY ABSORBENT ARTICLE

(75) Inventors: Antonio Carlos Ribeiro Carvalho, Taubate (BR); Marcia Helena Teixeira Fajolli, Sao Jose dos Campos (BR); Flavia Guimaraes Guaragna, Pindamonhangaba (BR)

(73) Assignee: Johnson & Johnson Ind. E Com. Ltda (BR)

( * ) Notice: Subject to any disclaimer, the term of this patent is extended or adjusted under 35 U.S.C. 154(b) by 1750 days.

(21) Appl. No.: 10/040,575

(22) Filed: Nov. 1, 2001

(65) Prior Publication Data

US 2002/0128622 A1    Sep. 12, 2002

(30) Foreign Application Priority Data

Mar. 12, 2001   (BR) .................................. D6100490

(51) Int. Cl.
*A61F 13/15*    (2006.01)

(52) U.S. Cl. ......... 604/385.01; 604/385.02; 604/385.03; 604/386

(58) Field of Classification Search ............. 604/385.01, 604/385.03, 385.04, 386, 385.02
See application file for complete search history.

(56) References Cited

U.S. PATENT DOCUMENTS

| | | | |
|---|---|---|---|
| 2,787,271 A | 4/1957 | Clark | |
| 3,397,697 A | 8/1968 | Rickard | |
| 4,285,343 A | 8/1981 | McNair | |
| 4,589,876 A | 5/1986 | Van Tilburg | |
| 4,601,775 A | 7/1986 | Grone | |
| 4,608,047 A | 8/1986 | Mattingly | |
| 4,687,478 A | 8/1987 | Van Tillburg | |
| 4,900,320 A | 2/1990 | McCoy | |
| 4,917,697 A | 4/1990 | Osborn, III et al. | |
| 5,171,302 A | 12/1992 | Buell | |
| 5,391,162 A * | 2/1995 | Widlund et al. | 604/385.04 |
| 5,423,787 A * | 6/1995 | Kjellberg | 604/368 |
| 5,514,104 A | 5/1996 | Cole | |
| 5,575,786 A | 11/1996 | Osborn, III | |
| 5,713,886 A * | 2/1998 | Sturino | 604/390 |
| 5,807,365 A | 9/1998 | Luceri | |
| 5,919,181 A | 7/1999 | Visscher | |
| 6,004,893 A | 12/1999 | Van Tilburg | |
| D460,177 S | 7/2002 | Endo | |

(Continued)

FOREIGN PATENT DOCUMENTS

AU    7335581    3/1982

(Continued)

OTHER PUBLICATIONS

European Search report dated Apr. 8, 2004, for corresponding EP application 03001778.4.

(Continued)

*Primary Examiner* — Lynne Anderson

(57) ABSTRACT

A sanitary napkin including a central absorbent pad, the central absorbent pad having a liquid pervious cover layer, a liquid impervious barrier layer and an absorbent core between the cover layer and barrier layer. The central absorbent pad includes a pair of flaps adapted to fold over a crotch portion of an undergarment in use. The central absorbent pad further includes two preferential bending axes, each axis being inward from and adjacent to a respective longitudinal side edge and extending obliquely with respect to the longitudinal centerline, the axes converging towards the longitudinal centerline in the first distal end of the central absorbent pad. The preferential bending axes are adapted to enable the sanitary napkin to be folded from an initial substantially hourglass shape to a tapered shape.

10 Claims, 2 Drawing Sheets

U.S. PATENT DOCUMENTS

| | | | |
|---|---|---|---|
| 2002/0077618 A1* | 6/2002 | Molas | 604/385.201 |
| 2002/0128622 A1 | 9/2002 | Carvalho | |
| 2002/0138055 A1* | 9/2002 | Motta et al. | 604/385.01 |
| 2003/0083637 A1 | 5/2003 | Killeen | |

FOREIGN PATENT DOCUMENTS

| | | |
|---|---|---|
| CN | 1315168 A | 8/2000 |
| CN | 1406565 A | 4/2003 |
| DE | 200 02 192 U1 | 8/2000 |
| DE | 299 11 806 U1 | 12/2000 |
| DE | 201 14 825 U1 | 3/2002 |
| DE | 29917726 | 7/2002 |
| DM | 045 544 | 10/1998 |
| EP | 0 511 905 A1 | 11/1992 |
| EP | 0 511 905 B1 | 11/1992 |
| EP | 830120 A1 | 3/1998 |
| EP | 1 016 393 A1 | 7/2000 |
| EP | 1138295 A1 | 10/2001 |
| EP | 1138294 | 10/2004 |
| GB | 2081101 A | 2/1982 |
| GB | 2319730 A | 6/1998 |
| JP | 9220258 A | 8/1997 |
| RU | 2089151 C1 | 9/1997 |
| WO | 9114415 A1 | 10/1991 |
| WO | 9207537 A1 | 5/1992 |
| WO | 9602217 A1 | 2/1996 |
| WO | WO 96/38110 A1 | 12/1996 |
| WO | 0072790 A1 | 12/2000 |
| WO | 0135888 A1 | 5/2001 |
| WO | 0178637 A1 | 10/2001 |

OTHER PUBLICATIONS

European Search report dated Apr. 8, 2004, for corresponding EP application 03001779.2.

* cited by examiner

8,277,428 B2

SANITARY ABSORBENT ARTICLE

FIELD OF THE INVENTION

The present invention relates to disposable absorbent articles, such as sanitary napkins with side flaps and two preferential bending axes, each axis being inward from and adjacent to a respective longitudinal side edge and extending obliquely with respect to the longitudinal centerline, the axes converging towards the longitudinal centerline in the first distal end of the central absorbent pad.

BACKGROUND OF THE INVENTION

Sanitary napkins having side flaps are disclosed in the literature and are generally available in the marketplace. Generally, the flaps extend laterally from the side edges of a central absorbent structure and are intended to drape over the edges of the wearer's panties in the crotch region. Thus, the flaps are disposed between the edges of the wearers panties in the crotch region and the wearer's thighs. Commonly, the flaps are provided with an attachment means for affixing the flaps to the underside of the wearer's panties.

The flaps serve at least two purposes. First, the flaps prevent exudates from soiling the edges of the wearer's panties and second, the flaps, when affixed to the underside of the panties, help stabilize the napkin in the undergarment and prevent it shifting out of place.

Sanitary napkins having flaps are disclosed in U.S. Pat. No. 4,687,478, entitled "Shaped Sanitary Napkin With Flaps", to Van Tilburg on Aug. 18, 1987, U.S. Pat. No. 4,608,047, entitled "Sanitary Napkin Attachment Means", to Mattingly on Aug. 26, 1986, U.S. Pat. No. 4,589,876, entitled "Sanitary Napkin", to Van Tilburg on May 20, 1986, U.S. Pat. No. 4,285,343, entitled "Sanitary Napkin", to McNair on Aug. 25, 1981, U.S. Pat. No. 3,397,697, entitled "Disposable Sanitary Shield For Undergarments", to Rickard on Aug. 20, 1968, U.S. Pat. No. 2,787,271, entitled "Sanitary Napkin", to Clark on Apr. 2, 1957 and U.S. Pat. No. 4,900,320, entitled "Sanitary Napkin With Undergarment Gathering Flaps, to McCoy on Feb. 13, 1990, all of which are incorporated herein by reference in their entirety.

While sanitary napkins having flaps are commonly viewed as providing better protection against soiling as compared to sanitary napkins without flaps, these napkins commonly experience a problem that keeps them from being optimally effective.

SUMMARY OF THE INVENTION

It is an object of the present invention to provide a sanitary napkin having flaps that is adaptable for use in a variety of styles of women's undergarments, including briefs, bikinis, thongs, and the like.

In accordance with the present invention, there has been provided a sanitary napkin that is adapted to be worn in a user's undergarment. The sanitary napkin comprises a central absorbent pad, the central absorbent pad having a liquid pervious cover layer, a liquid impervious barrier layer and an absorbent core between the cover layer and barrier layer, a longitudinal centerline, a lateral centerline, a pair of opposite longitudinal side edges, a first distal end and an opposite second distal and a flap extending laterally outward from each longitudinal side edge along a line of juncture, each flap being substantially adjacent the lateral centerline and adapted to fold over a crotch portion of an undergarment in use, the central absorbent pad further comprising two preferential bending axes, each axis being inward from and adjacent to a respective longitudinal side edge and extending obliquely with respect to the longitudinal centerline, the axes converging towards the longitudinal centerline in the first distal end of the central absorbent pad.

These and other objects of the present invention will be more readily apparent when considered in reference to the following description and when taken in conjunction with the accompanying drawings. It is to be understood, however, that the drawings are provided for purposes of illustration only and not as a definition of the boundaries of the invention, for which reference should be made to the appending claims.

DETAILED DESCRIPTION

The present invention relates to sanitary napkins adapted to be worn in a crotch portion of a wearer's undergarment in use. The napkin comprises a central absorbent pad having a liquid pervious cover layer, a liquid impervious barrier layer and an absorbent core between the cover layer and barrier layer. The central absorbent pad 12 will generally have an absorbent capacity sufficient to absorb the anticipated total amount of menstrual fluid. Central absorbent pad 12, is preferably thin, i.e. less than about 5 mm in caliper. It has been found that a sanitary napkin having a narrow, thin absorbent core is extremely comfortable to the user.

The central absorbent pad has a longitudinal centerline, a lateral centerline, a pair of opposite longitudinal side edges, a first distal end, an opposite second distal and a central region intermediate the first distal end and the second distal end. The napkin is provided with side flaps that are adapted to be folded over the edges of a crotch portion of the wearer's undergarment in use. Each flap extends laterally outward from each longitudinal side edge along a line of juncture. The central absorbent pad further comprises two preferential bending axes, each axis being inward from and adjacent to a respective longitudinal side edge from at least the central region of the central absorbent pad to the first distal end. The preferential bending axes extend obliquely with respect to the longitudinal centerline and converge towards the longitudinal centerline as they extend from the central region to the first distal end of the central absorbent pad.

As used herein, the term "sanitary napkin" refers to an article which is worn by females in an undergarment adjacent to the pudendal region and which is intended to absorb and contain the various exudates which are discharged from the body (e.g., blood menses, and urine) and which is intended to be discarded after a single use (i.e., it is not intended to be laundered or otherwise restored or reused).

Figure 1:
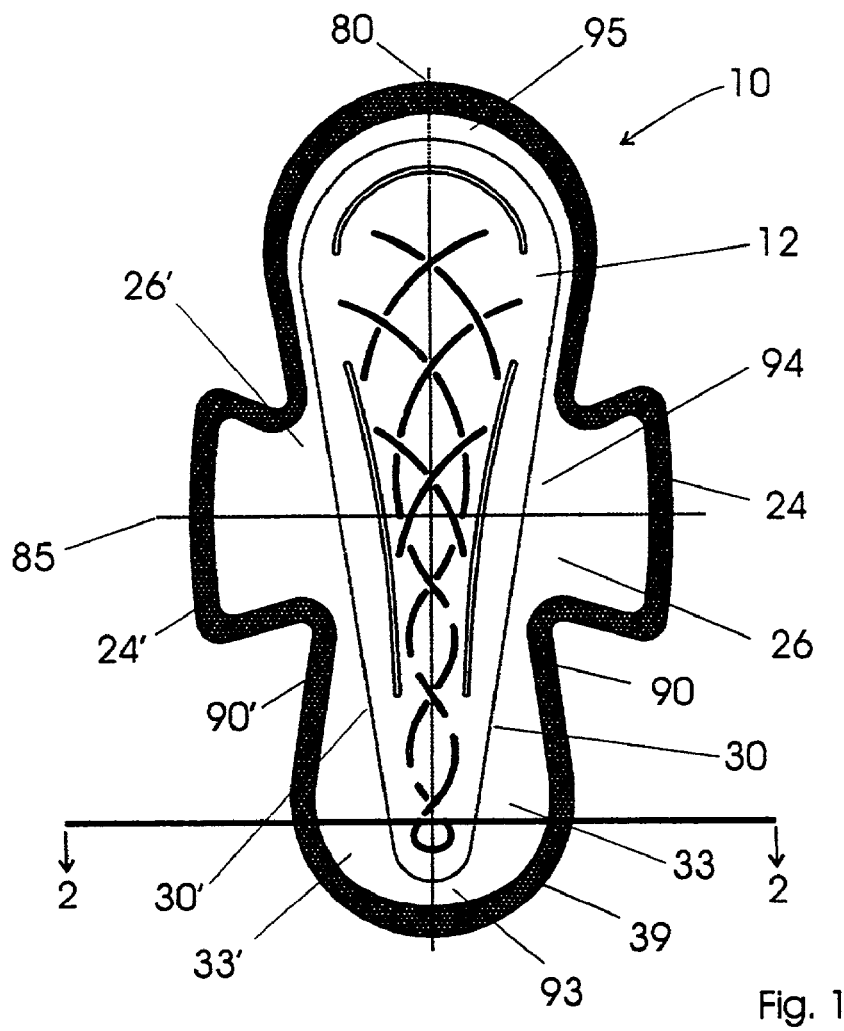
FIG. 1 is a top plan view of a sanitary napkin according to the present invention.
Figure 2:
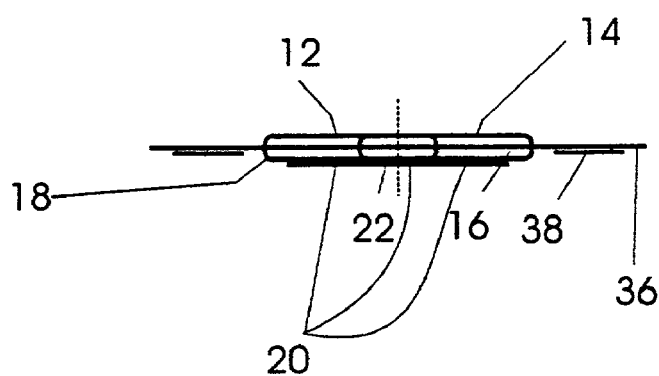
FIG. 2 is a side cut away view of the sanitary napkin of FIG. 1 taken through lines 2-2.

A specific example of implementation of a sanitary napkin according to the present invention is illustrated in FIG. 1. The sanitary napkin designated by the reference numeral 10 basically comprises a main body represented by central absorbent pad 12. The central absorbent pad 12 has an imaginary longitudinal centerline 80, an imaginary lateral centerline 85, a pair of opposite longitudinal side edges 90, 90', a first distal end 93 and an opposite second distal end 95 and a central region 94, intermediate the distal ends. Topsheet 14 and backsheet 18 are joined at seam 39 (also commonly referred to as a flange seal) around the entire periphery of sanitary napkin 10. The purpose of this seam is to unite the various elements of the sanitary napkin into a unitary structure. Seam 39 can be formed by any means commonly used in the art for this purpose such as by gluing, crimping, or heat-sealing. Seam 39 is illustrated extending completely around the periphery of sanitary napkin 10; this is suitable for ease of construction. However, other means of uniting the various elements can be used. As shown in FIG. 2, central absorbent pad 12 comprises absorbent core 16, topsheet 14 and backsheet 18, wherein backsheet 18 is disposed on a side of absorbent core 16 that is opposite that of topsheet 14.

Topsheet 14 is liquid permeable and, when sanitary napkin 10 is in use, is in close proximity to the skin of the user. Topsheet 14 is compliant, soft feeling, and non-irritating to the user's skin. It can be made from any of the materials conventional for this type of use. Non-limiting examples of suitable materials that can be used as topsheet 14 are woven and nonwoven fabrics formed from polyester, polypropylene, nylon, and/or rayon fibers or the topsheet may be an apertured thermo-plastic film. Apertured formed films are preferred for topsheet 14 because they are pervious to liquids and yet non-absorbent. Thus, the surface of the formed film that is in contact with the body remains dry and is more comfortable to the wearer.

Backsheet 18 is impervious to liquids and, thus, prevents menstrual fluid from soiling the clothing of the user. Any material used in the art for such purpose can be utilized herein. Suitable materials include embossed or non embossed polyethylene films and laminated tissue.

Figure 3:
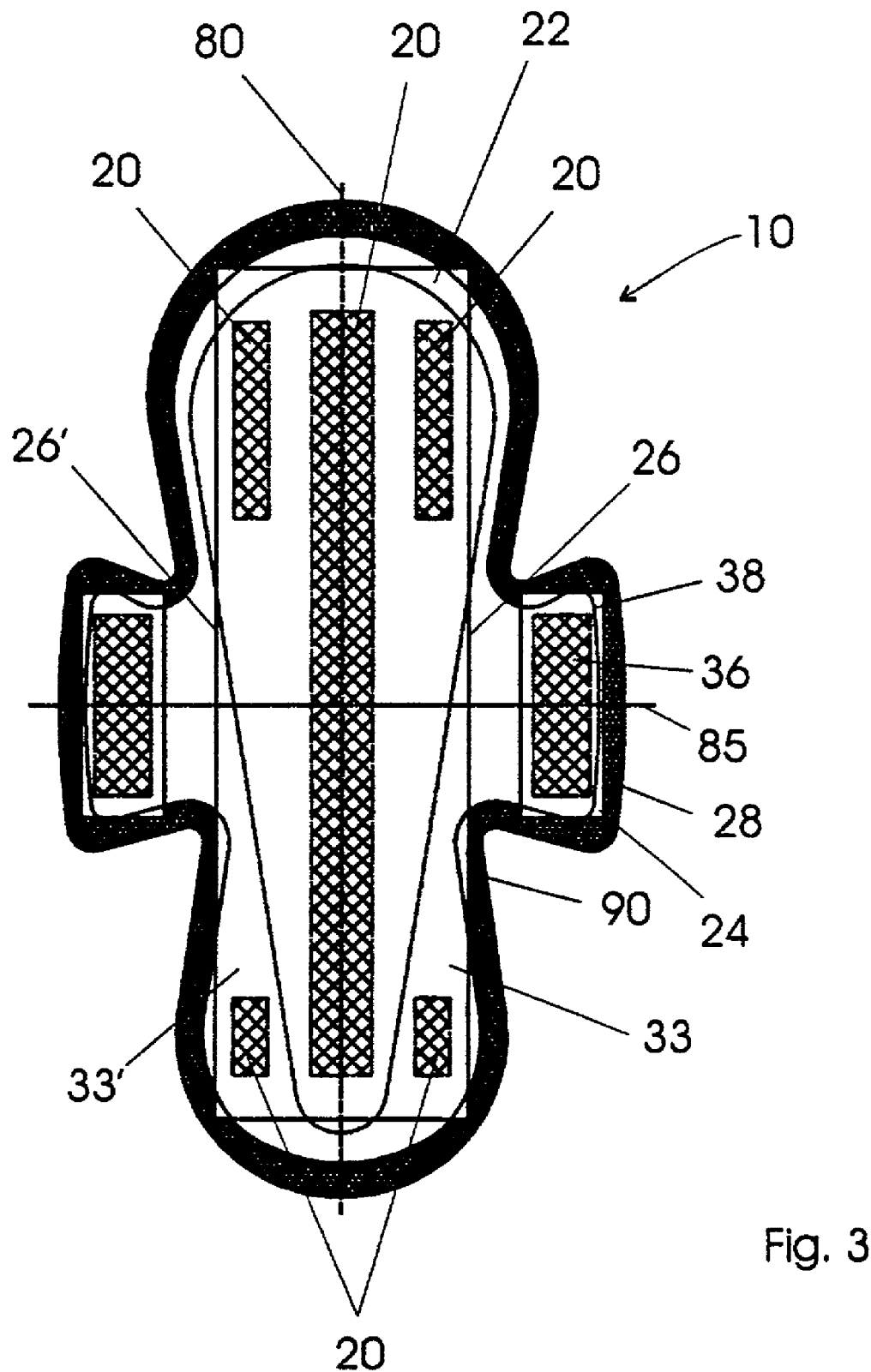
FIG. 3 is a bottom plan view of a sanitary napkin according to the present invention.

Absorbent core 16 provides the means for absorbing menstrual fluid. Absorbent core 16 is generally compressible, comfortable and non-irritating to the user's skin. It can comprise any material used in the art for such purpose. Examples include comminuted wood pulp that is generally referred to as airfelt, creped cellulose wadding, absorbent foams, absorbent sponges, absorbent hydrogel materials, polymeric fibers, or any equivalent material or combinations of materials. In a preferred embodiment, as shown in FIGS. 1 and 3, the absorbent core 16 is wider in the second distal end 95 and tapers continuously towards the first distal end 93. By tapering the absorbent core 16 yet maintaining substantially the same width of the other components in the central absorbent pad 12, a pair of opposite preferential bending axes 30, 30' are formed along the edges of the absorbent core in the region from at least the central region 94 to the first distal end 93.

In an alternative embodiment (not shown) the longitudinally extending side edges of the absorbent core extend substantially parallel to and slightly inward from the longitudinal side edges of the central absorbent pad. In accordance with this embodiment, the preferential bending axes may be formed by embossing the absorbent core to form longitudinally extending channels that are capable of acting as a hinge.

Referring now to FIGS. 2 and 3, the portion of the outer surface of backsheet 18 that is generally in vertical registration with absorbent core 16 is provided with central absorbent pad adhesive 20. Central absorbent pad adhesive 20 provides an adhesive attachment means for securing central absorbent pad 12 to the crotch portion of a undergarment. Any adhesive or glue used in the art for such purpose can be used herein, with pressure-sensitive adhesive being preferred. Suitable adhesives are Century A-305IV manufactured by the Century Adhesives Corporation and Instant LOK 34-2823 manufactured by National Starch Company. The central absorbent pad adhesive may be the same width as absorbent core, or as shown in FIG. 3 it may be a plurality of relatively narrow stripes. However, the width is not critical and appropriate widths, as well as lengths, can be readily selected by those skilled in the art. The pressure-sensitive adhesive of central absorbent pad adhesive 20 should be covered with central absorbent pad liner 22 to keep the adhesive from drying out and to keep it from sticking to extraneous surfaces prior to use. Any commercially available release liner commonly used for such purposes can be used herein. Nonlimiting examples of suitable release liners are BL30MG-A SILOXE1/0 and BL 30 MG-A SILOX 4/P/O both of which are manufactured by the Akrosil Corporation.

As can be observed from the foregoing, central absorbent pad 12 comprises an absorbent core having an upper surface covered by a fluid pervious body contacting surface (represented in FIG. 2 by topsheet 14) and an opposed liquid impervious surface (represented in FIG. 2 by backsheet 18). It is to be understood that the embodiment illustrated is only one possible embodiment. Other possible embodiments include one in which an absorbent core is essentially completely wrapped with topsheet before it is placed on a backsheet. The absorbent core can also comprise an absorbent layer which possesses sufficient integrity to stand-alone and which is fluid permeable on one surface while the other surface has been treated to render it liquid impervious.

It should be noted that a relatively narrow central absorbent pad 12 is effective because the overall configuration and use of sanitary napkin 10 results in central absorbent pad 12 being maintained in close proximity to the body. Such proximity of central absorbent pad 12 places it precisely where it should be: very near the body at the vaginal opening. Central absorbent pad 12 can then absorb the vast majority of the menstrual fluid (menses) before it has an opportunity to flow along the central absorbent pad 12. As shown in FIG. 1, the absorbent core 16 is generally tapered from a relatively wide distal end region to a relatively narrow opposite distal end region so as to conform generally to the wearer's thighs and to be easily conformable to a variety of undergarment styles. The width of the wider second distal end is preferably less than 75 mm, more preferably from about 60 mm to 70 mm. Generally, the width of a central portion of the crotch portion of an undergarment is from about 45 mm to about 75 mm. It is preferred that the width of the central region 94 of the central absorbent pad 12 is less than or equal to the width of the undergarment in this region. The width of the absorbent core preferably continuously tapers from the second distal end toward the first distal end, the first distal end having a width of less than 30 mm, preferably about 15 to 20 mm. While the taper is illustrated as being a substantially straight line and such constitutes a preferred embodiment, other variations are considered to be within the scope of the present invention such as curved or arcuate lines. In use, if the wearer chooses an undergarment style such as a brief style, both of the distal end regions of the sanitary napkin remain substantially planar within the undergarment, and thus remain in contact with the wearer's body. However, if the undergarment style is a thong or tanga type undergarment, then the sanitary napkin of the present invention is adapted to fold along the preferential bending lines 30, allowing the relatively narrow distal end region of the absorbent core to remain on a body-facing side of the wearer's undergarment while the side margins 33, 33' of the first distal end region of the central absorbent pad comfortably fold around the edges of the undergarment. The side margins should have a lateral dimension sufficient to enable the side margin to be folded around the edges of the undergarment. Accordingly, the side margins have a lateral dimension as measured from the preferential bending line 30 to the longitudinal side edge 90 in the first distal end that is sufficient to allow the side margin to fold over the edges of a thong style undergarment in use. In general, a lateral dimension of at least 7 mm has been found to be sufficient and the lateral dimension is preferably about 10 to 20 mm. As shown in FIG. 3, it is preferred that the side margins 33, 33' have an adhesive attachment means 20 on a garment faceable side of the backsheet that is adapted to allow a wearer to adhesively affix the side margins to their undergarment in use.

The central absorbent pad 12 has two flaps 24 and 24' extending laterally outward from the longitudinal side edges of the central absorbent pad 12 in a central portion thereof adjacent the lateral centerline. As shown in FIG. 1 flaps 24 and 24' extend substantially along the lateral centerline 85. As used herein, the terminology "central portion" and "lateral centerline" refer generally to a region of the central absorbent pad 12 that is intended to be placed in a crotch portion of a wearer's undergarment. Thus, for some embodiments of the invention wherein the sanitary napkin is asymmetrical, such as in a product intended for overnight use, the central portion and lateral centerline may not be located in the exact geometric center of the central absorbent pad. While it is not necessary that the flaps be mirror images of one another they preferably are. Topsheet 14 forms one surface of flaps 24, 24' while backsheet 18 forms the other surface. In general, the flaps do not require a topsheet to enable them to function properly, but the use of a topsheet is preferred. Flap topsheet can be integral with the central absorbent body, as illustrated, or it can be an independent element; the former being preferred. All of the specific physical properties of the topsheet 14 previously described, apply to any flap topsheet that is used. There is, however, no requirement that the flap topsheet be the same material as the topsheet associated with the central absorbent pad. In one possible embodiment, the flap topsheet may be nonwoven material while the topsheet over the central absorbent pad is an apertured polymeric film. In the embodiment illustrated in FIG. 2, backsheet 18 serves as a backsheet for flaps 24 and 24'. The flaps require a backsheet (or more generally, a liquid impervious materials) to enable them to function properly. The flap backsheet can be integral with the absorbent core liquid impervious surface or they can be independent elements. All of the specific physical properties of the backsheet 18 previously described apply to the flap backsheet.

At least a portion of the outer, garment faceable surface of flap 24, in a region adjacent distal edge 78, is coated with flap adhesive 36. Flap adhesive 36 is an adhesive attachment means which is used to assist in maintaining flap 24 in position after it is wrapped around the edge of the crotch portion of the undergarment as described below. Any adhesive used for central absorbent pad adhesive 20 can be used as flap adhesive 36. Also, flap adhesive 36 is covered with a removable flap release liner 38. Any release liner material used for central absorbent pad release liner 22 can be used for flap release liner 38. Each flap 24, 24' is associated with central absorbent pad 12 along a line of juncture 26. As used herein, the term "line of juncture" refers to any of various curved or straight lines. Each flap 24, 24' has a distal edge 78 that is remote from a proximal edge defined by the line of juncture 26.

It is to be observed that lines of juncture 26 and 26' are the lines along which flaps 24 and 24' are associated with the absorbent core (represented by central absorbent pad 12); as such they represent lines of demarcation between the absorbent core and the flaps. In the embodiment shown in FIGS. 1 and 3, the lines of juncture 26, 26' are coincident with the preferential bending lines 30, 30' in the central region 94 of the central absorbent pad 12.

The sanitary napkin shown in FIGS. 1 and 2 has a substantially linear line of juncture 26. The precise shape of flap 24, as well as the overall shape of the sanitary napkin 10 can be selected by those skilled in the art without undue experimentation. In the embodiment illustrated in FIG. 1, the flaps are symmetrically disposed along the longitudinal axis of the sanitary napkin.

The sanitary napkin of the present invention, such as the one illustrated in FIGS. 1-3, is utilized by removing the release liners 22 and 38 and 38' and thereafter placing the sanitary napkin in a undergarment. The center region of central absorbent pad 12 is placed in crotch portion (not shown) of the undergarment with one end of central absorbent pad 12 extending towards the front section of the undergarment and the other end towards the back section and with the backsheet 18 in contact with the inner surface of center crotch portion of the undergarment. Central absorbent pad adhesive 20 maintains central absorbent pad 12 in position. The distal portions of flaps 24 and 24' are folded around, respectively, side edges and of the crotch portion of the undergarment. Flap adhesive 36 and 36' secure flaps 24 and 24' in such position, thus, flaps 24 and 24' are each folded over themselves with a portion of the undergarment.

What is claimed is:

1. A sanitary napkin comprising:
   a central absorbent pad, the central absorbent pad having a liquid pervious cover layer, a liquid impervious barrier layer and an absorbent core between the cover layer and barrier layer, a longitudinal centerline, a lateral centerline, a pair of opposite longitudinal side edges, a first distal end and an opposite second distal end, a flap extending laterally outward from each longitudinal side edge along a line of juncture, each flap extending substantially along the lateral centerline and adapted to fold over a crotch portion of an undergarment in use,
   said core being continuously tapered from the second end towards the first end, the barrier and the cover extending beyond the core,
   the central absorbent pad further comprising two preferential bending axes, each preferential bending axis being defined by a respective edge of the core, each axis being inward from and adjacent to a respective longitudinal side edge and extending obliquely with respect to the longitudinal centerline, the axes converging towards the longitudinal centerline in the first distal end of the central absorbent pad,
   wherein the central absorbent pad has a pair of opposite side margins, each side margin being adjacent a respective preferential bending line and adapted to fold along said respective preferential bending line, each side margin being capable of being folded over an edge of a wearer's undergarment in use, and
   wherein said napkin has a first configuration wherein said napkin is structured and arranged to be used with a brief style undergarment and a second configuration wherein said side margins are in a folded condition such that said napkin is structured and arranged to be used with a thong style undergarment.

2. A sanitary absorbent article as defined in claim 1, wherein said preferential bending axes extend from the lateral centerline to the first distal end.

3. A sanitary absorbent article as defined in claim 1, wherein said preferential bending axes extend from the second distal end to the first distal end.

4. A sanitary absorbent article as defined in claim 1, wherein the first distal end has a width of less than 30 mm.

5. A sanitary absorbent article as defined in claim 1, wherein the first distal end has a width of about 15 mm to 20 mm.

6. A sanitary absorbent article as defined in claim 1, wherein each side margin has an adhesive attachment means on a garment faceable side thereof that is adapted to allow a wearer to adhesively affix the side margins to their undergarment in use.

7. A sanitary absorbent article as defined in claim 1, wherein the side margins have a lateral dimension as measured from the preferential bending line to the longitudinal side edge of at least 7 mm.

8. A sanitary absorbent article as defined in claim 1, wherein the side margins have a lateral dimension as measured from the preferential bending line to the longitudinal side edge is preferably about 10 to 20 mm.

9. A sanitary absorbent article as defined in claim 1, wherein said two preferential bending axes are structured and arranged to permit at least a portion of said central absorbent pad to be folded along a respective one of said preferential bending axes.

10. A sanitary absorbent article as defined in claim 9, wherein said portion of said central absorbent pad folded along said respective one of said preferential bending axes is structured and arranged to alter said central absorbent pad from an initial substantially hourglass shape to a tapered shape.

* * * * *